US012551651B2

(12) United States Patent
Walls et al.

(10) Patent No.: US 12,551,651 B2
(45) Date of Patent: Feb. 17, 2026

(54) HUMIDIFICATION APPARATUS

(71) Applicant: Fisher & Paykel Healthcare Limited, Auckland (NZ)

(72) Inventors: Bruce Michael Walls, Auckland (NZ); Melissa Catherine Bornholdt, Auckland (NZ); Peter Lawrence Grylls, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 864 days.

(21) Appl. No.: 17/634,489

(22) PCT Filed: Aug. 20, 2020

(86) PCT No.: PCT/NZ2020/050090
§ 371 (c)(1),
(2) Date: Feb. 10, 2022

(87) PCT Pub. No.: WO2021/034202
PCT Pub. Date: Feb. 25, 2021

(65) Prior Publication Data

US 2022/0288345 A1 Sep. 15, 2022

Related U.S. Application Data

(60) Provisional application No. 62/889,288, filed on Aug. 20, 2019.

(51) Int. Cl.

| | |
|---|---|
| ***A61M 16/16*** | (2006.01) |
| ***A61M 16/00*** | (2006.01) |
| ***A61M 16/10*** | (2006.01) |

(52) U.S. Cl.
CPC ...... *A61M 16/162* (2013.01); *A61M 16/0066* (2013.01); *A61M 16/109* (2014.02); (Continued)

(58) Field of Classification Search
CPC .................................................. F24F 6/00–18
See application file for complete search history.

(56) References Cited

U.S. PATENT DOCUMENTS

| | | | |
|---|---|---|---|
| 8,555,879 | B2 | 10/2013 | Potharaju et al. |
| 10,124,143 | B2 | 11/2018 | Smith et al. |

(Continued)

FOREIGN PATENT DOCUMENTS

| | | |
|---|---|---|
| EP | 3043854 | 7/2016 |
| EP | 3178513 | 6/2017 |

(Continued)

*Primary Examiner* — Kendra D Carter
*Assistant Examiner* — Mautin I Ashimiu
(74) *Attorney, Agent, or Firm* — VIA LLP

(57) ABSTRACT

The present invention relates to a humidification apparatus having a compartment that receives a removable humidification chamber. The apparatus has an actuator that can be operated by a user to move the humidification chamber from an operating position to a releasing position. In the operating position the humidification chamber is received by the humidification compartment and forms a portion of the flow path through the humidification apparatus. In the releasing position the humidification chamber is displaced outwardly from the operating position so that a user can more easily remove the humidification chamber from the apparatus.

24 Claims, 8 Drawing Sheets

(52) U.S. Cl.
CPC ............... *A61M 2205/3653* (2013.01); *A61M 2205/8243* (2013.01)

(56) References Cited

U.S. PATENT DOCUMENTS

| | | | | |
|---|---|---|---|---|
| 2008/0245365 | A1* | 10/2008 | Genger ................. | A61M 16/16 392/394 |
| 2015/0115483 | A1* | 4/2015 | Miller ................. | A61M 16/024 261/142 |
| 2016/0310691 | A1 | 10/2016 | Bath et al. | |
| 2017/0348505 | A1 | 12/2017 | Doo et al. | |
| 2017/0361053 | A1* | 12/2017 | Dimatteo ............ | A61M 16/024 |
| 2018/0161532 | A1 | 6/2018 | Klasek et al. | |
| 2020/0368468 | A1* | 11/2020 | Liu ....................... | A61M 16/16 |

FOREIGN PATENT DOCUMENTS

| | | |
|---|---|---|
| EP | 3381496 | 10/2018 |
| JP | 2005276676 | 10/2005 |
| JP | 2006016813 | 1/2006 |
| KR | 20110026082 | 3/2011 |
| RU | 101357 | 1/2011 |
| WO | WO 2007/019625 | 2/2007 |
| WO | WO 2008/056993 | 5/2008 |
| WO | WO 2010/031126 | 3/2010 |
| WO | WO 2010/140903 | 12/2010 |
| WO | WO 2011/087113 A1 | 7/2011 |
| WO | WO 2012/135912 | 10/2012 |
| WO | WO 2015/038014 | 3/2015 |
| WO | WO 2016/089224 | 6/2016 |
| WO | WO 2020/082317 | 4/2020 |
| WO | WO 2020/096468 A1 | 5/2020 |

* cited by examiner

HUMIDIFICATION APPARATUS

RELATED APPLICATION

The present application claims priority to U.S. of America Provisional Patent Application No. 62/889,288 filed on Aug. 20, 2019, the full contents of which are hereby incorporated in the present specification by direct reference.

FIELD OF THE INVENTION

The present invention relates to a humidification apparatus that can be used to humidify a gas stream. A humidified gas stream can be delivered to a patient for respiratory assistance, such as for Positive Airway Pressure (PAP) therapy.

BACKGROUND

Humidification apparatus often have a humidification chamber containing an amount of water. The gas stream is humidified as it passes through the humidification chamber. To make the process of emptying, cleaning and refilling the humidification chamber convenient for a user, the chamber is usually removable from the rest of the apparatus. A problem with existing apparatus is that removing the humidification chamber can be physically demanding, especially for users with poor finger dexterity. There is therefore a need for an alternative apparatus where it is intuitive and/or relatively straightforward to insert and remove the chamber from the apparatus.

SUMMARY OF THE INVENTION

One aspect of the present invention relates to a humidification apparatus including:

- a blower for generating a gas stream;
- a removable humidification chamber for containing water;
- a humidification compartment that receives the humidification chamber; and
- an actuator that can be operated by a user to move the humidification chamber from: an operating position in which the humidification chamber is received by the humidification compartment and in which a flow path, that includes a portion extending through the humidification chamber, is provided for the gas stream; to a releasing position in which the humidification chamber is displaced outwardly from the operating position and in which the user can remove the humidification chamber from the apparatus.

The flow path may include a first portion extending from the blower and a second portion extending to an apparatus outlet port. The first and second portions of the flow path may be present irrespective of the position of the humidification chamber. When the humidification chamber is in the operating position, the flow path is completed through the apparatus from the blower to the apparatus outlet port.

Another aspect of the present invention relates to a humidification apparatus including:

- a blower for generating a gas stream;
- an apparatus outlet port to enable delivery of gas to a patient;
- a removable humidification chamber for containing water;
- a humidification compartment that receives the humidification chamber;

- a flow path through the apparatus from the blower to the apparatus outlet port; and
- an actuator that can be operated by a user to move the humidification chamber from: an operating position in which the humidification chamber is received by the humidification compartment and in which the humidification chamber forms a portion of the flow path through the humidification apparatus; to a releasing position in which the humidification chamber is displaced outwardly from the operating position and in which the user can remove the humidification chamber from the apparatus.

The apparatus may have a powered device that is operable when the humidification chamber is in the operating position to heat water in the humidification chamber.

The actuator may locate the powered device relative to the humidification chamber in the operating position so that the powered device is operable.

The humidification chamber may have a thermally conductive heater base, the humidification compartment may have a heater element, and the actuator presses the heater element against the heater base when the humidification chamber is in the operating position.

The humidification compartment may have a flow path outlet port, hereinafter referred to as the outlet port, that is in communication with the outlet of a blower that generates the stream of breathable gas.

The apparatus outlet port may be a housing outlet port. For instance, the housing outlet port may be on the humidification compartment.

The apparatus outlet port may be on the humidification chamber. For example, on a lid of the humidification chamber.

The humidification compartment may have a flow path inlet port, hereinafter referred to as the inlet port, that can communicate with a gas stream conduit for supplying the gas stream to a user, or an apparatus outlet port to which the gas stream conduit may be connected.

The humidification chamber may have a chamber inlet and a chamber outlet, in which the chamber inlet communicates with the outlet port and the chamber outlet communicates with the inlet port.

When the humidification chamber is in the operating position, the flow path is sealed and extends from the blower, through the humidification chamber, to the apparatus outlet port or the gas stream conduit.

The first portion of the flow path may be sealed to the humidification chamber when in the operating position.

The second portion of the flow path may be sealed to the humidification chamber when in the operating position. The second portion may be located in a housing. The housing may define the humidification compartment, and the apparatus outlet port may be on the housing.

When the apparatus outlet port is on the humidification chamber, the second portion of the flow path may be located in the humidification chamber.

In the releasing position, the first portions of the flow path may be broken from the humidification chamber.

In the releasing position, the second portion of the flow path may be broken from the humidification chamber. That is to say, the flow path between the humidification chamber and the first and second portions of the flow path may be no longer sealed when the humidification chamber is in the releasing position. When the flow path is broken, effective flow communication between the humidification chamber and the humidification compartment is absent.

The apparatus may also include a moving base to which the actuator is operably connected, and the humidification chamber can move from the operating position to the releasing position whilst seated on the base.

In one example, the user may manually move the humidification chamber from the releasing position to the operating position. In this situation the actuator may be inactive, such as turned off, disconnected, or the actuator may have a passive mode. The actuator may also have an active force or resistance, and the user pushes the humidification chamber against the actuator.

In another example, the user may also operate the actuator to move the humidification chamber from the releasing position to the operating position.

The humidification chamber may move upwardly and downwardly between the releasing position and the operating position.

The humidification compartment may have a recess having an upwardly facing opening, hereinafter referred to as the upper opening, that receives the humidification chamber.

In one example, the base may move within the compartment as the humidification chamber moves between the releasing position and the operating position.

The humidification chamber moves a release distance between the operating position and the releasing position. The release distance may be in the range of 2 to 20 cm, suitably in the range of 3 to 10 cm, and even more suitably in the range of 4 to 10 cm.

In the operating position, the humidification chamber defines another part of the flow path.

In the operating position, the humidification chamber may be located so as not to protrude from the humidification compartment. In one example, an outer surface of the humidification chamber, such as a chamber lid, may be flush with the humidification compartment in the operating position.

In the operating position, the humidification chamber may be located within the humidification compartment.

The humidification chamber may have a gripping section that protrudes from the humidification compartment when the humidification chamber is in the releasing position. In other words, in the releasing position, the gripping section of the humidification chamber protrudes from the humidification compartment so that the user can manually remove the humidification chamber from the compartment by holding the gripping section.

In the operating position, the gripping section may be located within the humidification compartment. That is to say, the gripping section may be obscured from view.

The gripping section may include a portion of an outer side wall of the chamber that extends outwardly of an opening of the humidification compartment.

The gripping section may include an upper peripheral portion of the outer side wall of the chamber.

The gripping section may include a cover on the humidification chamber.

The gripping section may have a finger recess that is sized to receive fingertips of the user.

The gripping section may have a friction surface that has a higher friction to a user's hand relative to adjacent surfaces of the humidification chamber. For example, the friction inducing surface may have formations such as corrugations, ridges, troughs and ribs.

The gripping section may also have a resiliently compressible material, for example, a rubberized material, closed cell foam, or a material containing silicone.

The gripping section may include at least one handle extending from the humidification chamber.

The actuator may be operable by a user to control movement of the base to move the humidification chamber from the operating position to the releasing position.

The actuator may be operable by a user to control movement of the humidification chamber located on the base from the operating position, in which the humidification chamber is located so as not to protrude from the humidification compartment, to the releasing position, in which the humidification chamber protrudes from the humidification compartment.

The actuator may be operable to move the base over the release distance.

For example, the actuator may be operable to move the base, and in turn the humidification chamber, over a range from 1 to 20 cm (i.e., 0.39 to 7.86 inches) between the operating position and the releasing position. Even more suitably the actuator may be operable to move the base, and in turn the humidification chamber, over a range of 2 to 10 cm, 3 to 10 cm, or 4 to 10 cm, or 4 to 6 cm (i.e., 1.57 to 2.36 inches).

The user may operate the actuator by applying a first pressing force to the humidification chamber which moves the humidification chamber from the releasing position into the operating position. The actuator may also be selectively operated by the user to move the humidification chamber from the operating position into the releasing position.

The actuator may be any suitable non-powered actuator, such as a biasing device that biases the base to move the humidification chamber from the operating position toward the releasing position.

The biasing device may be loaded when the humidification chamber is in the operating position and relatively unstressed when the humidification chamber is in the releasing position. When the biasing device is loaded, the biasing device is stressed, and when unloaded, the device is relatively unstressed.

The biasing device may be unstressed when the humidification chamber is in the operating position and the releasing position, and the biasing device may be relatively loaded when transitioning between the operating and the releasing positions.

The actuator may be selectively operated by the user to move the humidification chamber from the operating position to the releasing position by initially applying a second pressing force to the humidification chamber which moves the humidification chamber inwardly of the operating position, and then removing the second pressing force. Pressing the humidification chamber inwardly moves the humidification chamber further into the humidification compartment.

Once the second pressing force has been removed, the actuator is operable to move the base and in turn move the humidification chamber from the operating position to the releasing position.

The base may be held in a fixed position within the humidification compartment when the humidification chamber is in the operating position.

The biasing device may include any one or a number of devices such as: a compression spring, a tension spring, a torsion spring, a belleville spring, a gas strut, a pneumatic capacitor, a hydraulic capacitor, or scissor spring.

In one example the biasing device may include a plurality of springs arranged in parallel. For instance, the biasing device may include between 4 and 8 compression springs that are operably connected to the base.

In another example, the actuator may be any suitable powered actuator. Examples of suitable powered actuators include a power-driven screw ram, a power-driven car, a power-driven rack and pinion, and power-driven slider, a power-driven pulley and cable system, a power-driven piston and cylinder assembly or a power-driven cam assembly. In these examples, the power drive may be an electric drive, a pneumatic drive or hydraulic drive and so forth.

The actuator may be operated by a controller such as a button, switch or control knob that controls the movement of the base, and in turn, the movement of the humidification chamber between the operating position and the releasing position. For example, the controller may be used to control operation of the actuator when in the form of a powered actuator.

In another example, the base may move sideways between the operating position and the releasing position. For instance, the base may form part of a draw that moves horizontally. In this instance, the compartment may have an opening in a side wall that receives the humidification chamber. When the humidification chamber is located in the releasing position, the base may extend through the opening in the side wall, which enables a user to remove and replace the humidification chamber on the base manually. In this instance, the actuator may apply an active force or resistance in a horizontal plane.

The apparatus may include a powered device for heating water in the humidification chamber to increase or control humidification of the gas stream. The powered device may include a heater assembly including a heating element located within the humidification chamber and/or a heater plate that thermally engages the humidification chamber.

For example, the powered heater assembly may include a powered heater plate on the base that can be energized to heat, and the humidification chamber may have a thermally conductive heater base that sits on the heater plate for thermal engagement therebetween.

For example, the powered heater assembly may include a powered heating element arranged in the humidification chamber and an electrical coupling for electrically connecting the heating element to a power supply. The electrical coupling may be any suitable connector including couplings, sockets, shielded and unshielded couplings, couplings on leads and so forth.

The electrical coupling may be connected by locating the humidification chamber into the correct position on the base.

For example, the electrical coupling may include an electrically active central post on the base that is received by a socket on a bottom wall of the humidification chamber.

For example, the electrical coupling may have connectors on the humidification chamber and the humidification compartment that are electrically connected when the humidification chamber is received by the compartment in the operating position, and are electrically disconnected when the humidification chamber is in the releasing position.

For example, the connectors may be located on a sidewall of the humidification chamber and on a portion of the humidification compartment that faces the humidification chamber. Ideally, the connector on the humidification chamber is located at a height from a base of the humidification compartment. Having the electrical connection located on a sidewall of the humidification chamber, rather than on the bottom lower wall, may lower the risk of water ingress into the electrical connector.

In another example, the connector on the humidification chamber may be located at, or toward, a bottom wall of the humidification chamber and the connector on the humidification compartment is positioned to connect when the humidification chamber is in the operating position.

In an embodiment, the powered device may include an induction generator in the humidification compartment, and a co-operating heater base of the humidification chamber that heats on exposure to energy from the induction generator for heating the water in the humidification chamber. It will be appreciated that the term "induction generator" embraces a device that generators a high frequency alternating current through an electromagnet which generates a current in a target resistance material, such as the heater base of the humidification chamber, which in turn generates heat in the humidification chamber. An advantage in heating the water in the humidification chamber using induction is that the efficiency of heating the water is not dependent on conductive thermal engagement with the humidification chamber.

The apparatus may include a sealing assembly that seals the flow path, extending between the humidification compartment and the humidification chamber when the humidification chamber is in the operating position.

The sealing assembly may also provide a seal between the upper opening of the humidification compartment and the humidification chamber when the humidification chamber is in the operating position.

The sealing assembly may include a chamber sealing member extending about part of an outer wall of the humidification chamber. Suitably, the chamber sealing member is located about an upper part of the outer wall of the humidification chamber.

The chamber sealing member may be located about a perimeter of the upper part of the outer wall of the humidification chamber.

In one example the chamber sealing member may sealingly engage an inner wall of the humidification compartment when the humidification chamber is in the operating position.

The sealing assembly may include a compartment sealing member extending about the upwardly facing opening of the humidification compartment. Suitably, the compartment sealing member may be located about the upper opening of the humidification compartment.

The compartment sealing member may be located about a perimeter of the upper opening of the humidification compartment.

In one example, the compartment sealing member may sealingly engage the humidification chamber when the humidification chamber is in the operating position. In this situation, the humidification chamber may or may not have a chamber sealing member.

Similarly, it is possible for the compartment sealing member to be present without the chamber sealing member.

In one example, the chamber sealing member and the compartment sealing member may sealingly engage to seal the humidification compartment when the humidification chamber is in the operating position.

The chamber sealing member may be located on any suitable surface of the humidification chamber, including either one, or a combination of, an upright surface, a horizontal surface or an angled surface extending at an angle to the upright surface.

Similarly, the compartment sealing member may be located on any suitable surface of the humidification compartment, including either one, or a combination of, an upright surface, a horizontal surface or an angled surface extending at an angle to the upright surface.

The sealing assembly may also include flow path sealing members that seal the connection between the outlet port of the humidification compartment and the chamber inlet.

For instance, the sealing assembly may include at least one of:

i) an outlet port sealing member at the outlet port of the humidification compartment, and ii) an inlet sealing member at the chamber inlet.

Either one or both of the outlet port sealing member and the inlet sealing member may extend about the chamber inlet and the outlet port of the compartment, and seal the flow pathway extending between the humidification compartment and the humidification chamber when the humidification chamber is in the operating position.

The sealing assembly may include flow path sealing members that seal between the chamber outlet and the inlet port of the compartment.

For instance, the sealing assembly may include at least one of:

i) an inlet port sealing member at the inlet port of the humidification compartment, and ii) an outlet sealing member at the chamber outlet.

Either one or both of the inlet port sealing member and the outlet sealing member may extend about the inlet port of the compartment and the chamber outlet, and seal the flow path extending between the humidification compartment and the humidification chamber when the humidification chamber is in the operating position.

It will be appreciated that the flow path can be sealed by one or a combination of the sealing options as outlined above. For instance, the flow path may be sealed by one of the following:

a) A seal about the upper opening of the humidification compartment and the humidification chamber. One of the advantages of forming this seal is that the humidification compartment and the humidification chamber can both be pressurised to similar pressures, thereby enabling a degree of imperfection of the seal between the compartment outlet port and the chamber inlet, or a degree of imperfection in the seal between the compartment inlet port and the chamber outlet.

b) A seal about the compartment outlet port and the chamber inlet, and a seal about the compartment inlet port in the chamber outlet. One of the advantages of forming this seal is that the seal between the upper opening of the humidification compartment and the humidification chamber may be redundant.

c) A seal about the upper opening of the humidification compartment and the humidification chamber, and a seal about the compartment outlet port and the chamber inlet.

d) A seal about the upper opening of the humidification compartment and the humidification chamber, and a seal about the compartment inlet port and the chamber outlet.

The apparatus may have a first coupling device that acts between the humidification chamber and the humidification compartment.

The first coupling device may be operable to releasably lock the humidification chamber in the operating position.

The first pressing force may move the humidification chamber from the releasing position to the operating position and activate the first coupling device to releasably lock the humidification chamber in the operating position.

The first pressing force may move the humidification chamber inwardly of the operating position to operate/activate the first coupling device, and when the first pressing force has been removed, the actuator may cause the humidification chamber to move to the operating position where the humidification chamber is releasably locked.

The actuator may apply an active force or resistance toward an opening when the humidification chamber is in the operating position, and the first coupling device can secure the humidification chamber in position in the humidification compartment against the force, thereby pressing a heater plate against the humidification chamber. One advantage this provides is that the degree of thermal engagement between the heater plate and the humidification chamber can be increased by increasing the force applied by the actuator. The active force or resistance may act in the direction from the operating position to the releasing position. That is to say, when the humidification chamber moves upwardly and downwardly in the humidification compartment the active force can press the heater element upwardly onto the humidification chamber.

The humidification chamber may have has a thermally conductive heater base, the humidification compartment may have a heater element, and the apparatus may have at least one first coupling device that acts between the humidification chamber and the humidification compartment and is operable to releasably lock the humidification chamber in the operating position, and wherein the actuator applies an active force to the humidification chamber whilst the first coupling device secures the humidification chamber in the operating position against the active force, thereby pressing the heater element against the heater base.

The heater element may include a heater plate.

The first coupling device may be unlocked by action of the second pressing force moving the humidification chamber inwardly of the operating position.

The first coupling device has a movable locking member and a biasing member that biases the locking member toward a neutral position, and a fixed cam having working surfaces that are engaged by the locking member and moves the locking member away from the neutral position as the humidification chamber moves from the releasing position toward the operating position, and the working surfaces include a recessed surface that receives the locking member, and the locking member can be dislodged from the recessed surface by moving the humidification chamber inwardly into the humidification compartment.

In one example, the fixed cam may be located on an inner surface of the humidification compartment, and the locking member may be connected to the humidification chamber.

In this instance, the recessed surface of the fixed cam may face in an inward direction of the humidification compartment, such as toward the floor of the humidification compartment. In other words, the recessed surface may face in a direction that is parallel to movement of the humidification chamber moving from the releasing position to the operating position.

In another example, the locking member may be located on an inner surface of the humidification compartment, and the fixed cam may be connected to the humidification chamber.

In this instance, the recessed surface may face in an outward direction of the humidification compartment. In other words, the recessed surface may face in a direction that is parallel to movement of the humidification chamber moving from the operating position to the releasing position.

The biasing member may provide a resistive force that increases as the locking member slides over the fixed cam as the humidification chamber moves toward the operating position.

In addition, the actuator may also have an active force or resistance against which the user pushes when moving the humidification chamber toward the operating position.

The biasing member may urge the locking member into the recessed surface when the humidification chamber is in the operating position.

The actuator may assist in holding the locking member in the recessed surface of the fixed cam by the actuator applying active force or resistance to the humidification chamber in a direction from the releasing position to the operating position.

The actuator may be operable to move the humidification chamber from the operating position toward the releasing position when the first coupling device is deactivated.

The locking member may be a lug extending from the flexible arm.

A plurality of the first coupling devices may be arranged between the humidification chamber and the humidification compartment. In this instance, the first coupling devices may be evenly spaced about the humidification chamber and the humidification compartment.

The apparatus may include a second coupling device that acts between the base and the humidification compartment to releasably lock the position of the base when the humidification chamber is in the operating position.

The second coupling device may be released by the second pressing force moving the humidification chamber (and the base) inwardly, thereby allowing the actuator to move the base and the humidification chamber into the releasing position.

The second coupling device may include a lug connected to the actuator, the lug can be received by an opening when the humidification chamber is in the operating position, and the lug can be dislodged from the opening by the second pressing force.

The second coupling device may be connected to the biasing device.

The apparatus may have a lid that extends over the opening of the humidification compartment.

The lid may move between opened and closed positions and sealingly engage with the humidification compartment to enclose the compartment in the closed position. In one example, the lid may press against the humidification chamber so that the heater base is held to the heater element.

The humidification chamber may also have a chamber lid that can open and close the humidification chamber.

Another aspect of the present invention relates to a humidification apparatus including:

- a removable humidification chamber for containing water;
- a humidification compartment that receives the humidification chamber;
- a flow path for a gas stream; and
- a loader having an actuator and a base on which the humidification chamber can be placed, wherein the actuator can be operated by a user to move the base and move the humidification chamber from: i) an operating position in which the humidification chamber is received by the humidification compartment and communicates with the flow path to allow the gas stream to pass through the humidification chamber; to ii) a releasing position in which the humidification chamber can be removed from the humidification compartment by a user.

Another aspect of the present invention relates to a humidification apparatus including:

- a blower for generating a gas stream,
- a flow path for the gas stream,
- a humidification compartment that can receive a removable humidification chamber; and
- an actuator for moving the humidification chamber, wherein the actuator can be operated by a user to move the humidification chamber so that the humidification chamber moves from:
  - i) an operating position in which the humidification chamber is received by the humidification compartment and in which the flow path communicates with the humidification chamber so that the gas stream can pass therethrough; to
  - ii) a releasing position in which the humidification chamber is displaced outwardly from the operating position and in which the user can remove the humidification chamber from the humidification compartment.

Another aspect of the present invention relates to a humidification apparatus including:

- a blower for generating a gas stream;
- an apparatus outlet port to enable delivery of gas to a patient;
- a removable humidification chamber for containing water and including a thermally conductive heater base;
- a humidification compartment that receives the humidification chamber and including a heater element;
- a flow path through the apparatus from the blower to the apparatus outlet port; and
- an actuator to move the humidification chamber from: an operating position in which the humidification chamber is received by the humidification compartment and in which the humidification chamber forms a portion of the flow path through the humidification apparatus; to a releasing position in which the humidification chamber is displaced outwardly from the operating position and in which the user can remove the humidification chamber from the apparatus, and wherein the actuator biases the heater element against the heater base in the operating position.

The humidification apparatus described in any of the preceding three aspects may include any one or a combination of the features described herein.

Throughout this specification the terms "humidification compartment" and "compartment" are used interchangeably. Similarly, the terms "humidification chamber" and "chamber" are used interchangeably, and the terms "humidification apparatus" and "apparatus" are also used interchangeably.

BRIEF DESCRIPTION OF THE DRAWINGS

A preferred embodiment of the present invention will now be described with reference to the accompanying drawings which are summarized as follows.

DETAILED DESCRIPTION

Figure 1:
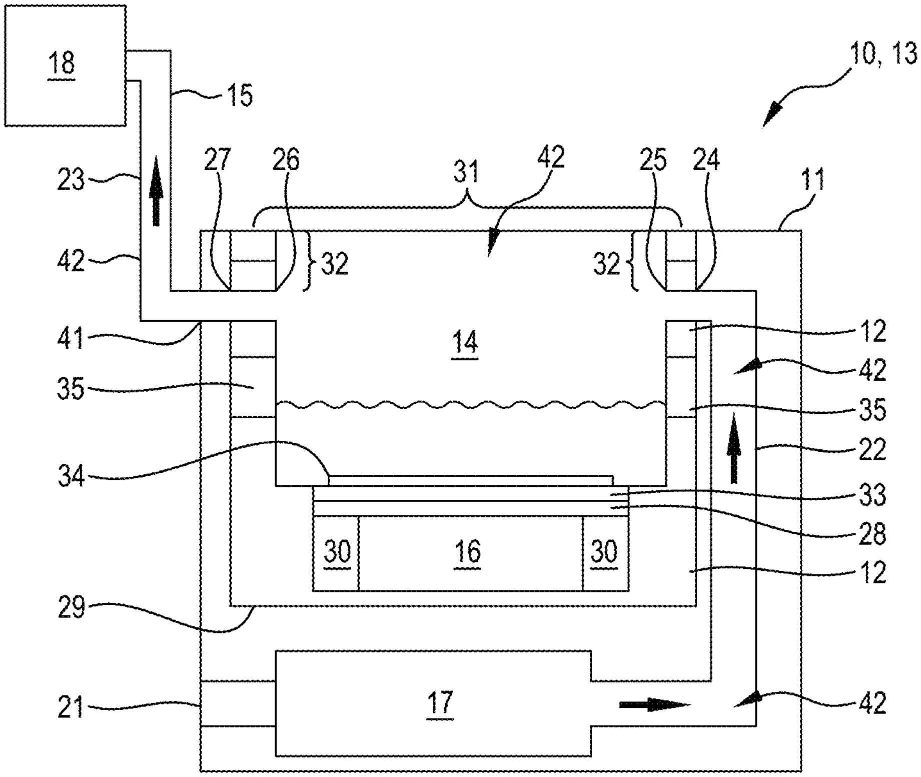
FIG. 1 is a schematic diagram of a respiratory device including an apparatus having a humidification compartment, a removable humidification chamber that is positioned within the compartment in an operating position, an actuator that is operable by a user to move the humidification chamber from the operating position to a release position, a blower for generating a stream of breathable gas, and a conduit for supplying the humidified gases stream to a user.

A preferred embodiment of the present invention will now be described in the following text which includes reference numerals that correspond to features illustrated in the accompanying figures. To maintain clarity of the figures however, all reference numerals are not included in each figure.

FIG. 1 is a schematic block diagram illustrating a respiratory device 10 comprising a humidification apparatus 11 including a humidification compartment 12, and a removable humidification chamber 14 that is received by the humidification compartment 12. The apparatus 11 has a housing 13 that contains a blower 17, and part of the housing defines the humidification compartment 12, including an upper opening 31 by which the humidification compartment 12 can receive the humidification chamber 14. The housing 13 also defines part of a flow path 42 for conveying a gas stream 15 from the blower 17. The humidification compartment 12 includes an actuator 16 that is operable by a user 18 to move the humidification chamber 14 from an operating position to a releasing position. The humidification chamber 14 is illustrated in the operating position in FIG. 1 and forms part of the flow path 42 in this position. The chamber 14 also contains an amount of water for humidifying the gas stream 15 passing through the humidification chamber 14. The humidification apparatus 11 also has a conduit 23 exiting from, or connected to, the housing 13 at a housing outlet port 41 that conveys a stream of humidified breathable gas to the user 18.

The housing 13 also has an air intake 21 in an outer wall from which the blower receives gases. An outlet of the blower is sealingly connected to a passageway 22 that extends to an outlet port 24. When the humidification chamber 14 is in the operating position, as shown in FIG. 1, the outlet port 24 communicates with a chamber inlet 25 so that the chamber inlet 25 is in flow communication with the blower 17.

The humidification chamber 14 also includes a chamber outlet 26 that communicates with an inlet port 27 of the humidification compartment 12, and the inlet port 27 communicates with a housing outlet 41 to which the conduit 23 is connected for conveying the stream of humidified gas to the user 18.

When the humidification chamber 14 is in the operating position, the outlet port 24 may connect to, or contact, the chamber inlet 25 and the inlet port 27 may connect to, or contact, the chamber outlet 26 thus providing flow communication. In other words, the humidification chamber 14 forms part of the flow path 42 when located in the operating position.

When the humidification chamber 14 is in the operating position, it is also possible that the outlet port 24 may be spaced from the chamber inlet 25 and/or the inlet port 27 may be spaced from the chamber outlet 26, and flow communication therebetween still occurs on account of sealing between the humidification compartment 12 and the humidification chamber 14, as shown for example, in FIGS. 14 to 17. However, it will be appreciated that the sealing between the humidification compartment 12 and the humidification chamber 14 may be provided even when the outlet port 24 seals to the chamber inlet 25, and the chamber outlet 26 seals to the inlet port 27.

The water level in the humidification chamber 14 can be replenished as required, and the humidification chamber 14 should also be cleaned to maintain hygienic standards. Both tasks are typically performed by the user 18 of the device 10, that is, by the patient rather than a health professional such as a doctor or a nurse, particularly when the device is being used in the home environment. However, as the user 18 is often elderly and may have impaired hand movement, for example, through other ailments such as arthritis, there is a need for the humidification chamber 14 to be readily removed and reloaded.

Figure 8:
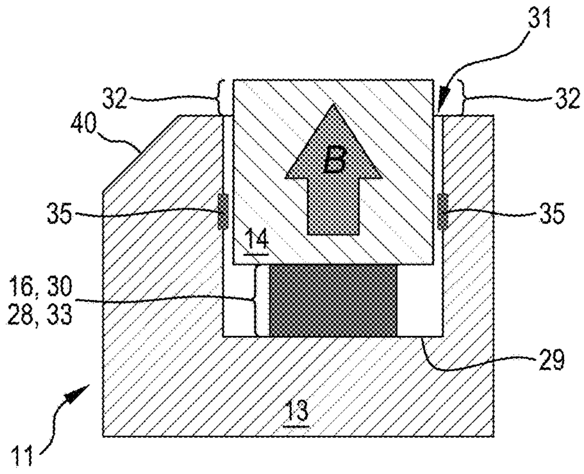
FIG. 8 is a schematic cross-sectional view of the apparatus shown in FIG. 7, in which the user has stopped applying the second pressing force and thereafter the actuator has moved the humidification chamber from the operating position to the releasing position.

To address this need, the actuator 16 of the apparatus 11 is controlled and operated by the user to move the humidification chamber 14 upwardly in the humidification compartment 12 from a lowered operating position to a raised releasing position. According to the preferred embodiment, the actuator 16 is an unpowered actuator 16 comprising a set of springs (not individually shown in the figures) that are arranged between a floor 29 of the humidification compartment 12 and a base 28 in order to bias the base 28 upwardly in the direction of arrow B, as shown in FIG. 8. In another embodiment, the actuator 16 may be a powered actuator, such as a slider driven by an electric motor.

Although not shown in the figures, the base 28 could be located in an aperture in the floor 29 of the compartment 12, and in the operating position, the base 28 could be located either in line with or below the level of the floor 29. In this arrangement, the actuator 16 could be located between a periphery of the base 28 and a perimeter of the aperture.

Figure 4:
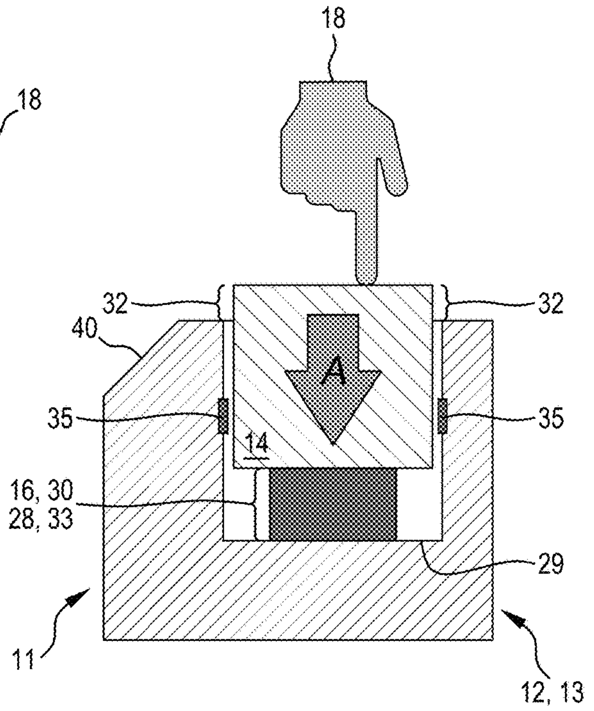
FIG. 4 is a schematic cross-sectional view of the apparatus shown in FIG. 3, in which the humidification chamber is located in a releasing position where the chamber is proud of the top of the compartment, and a user is applying a first pressing force in the direction of arrow A.

FIGS. 4 and 8 illustrate the humidification chamber 14 on the base 28 in the releasing position.

Figure 6:
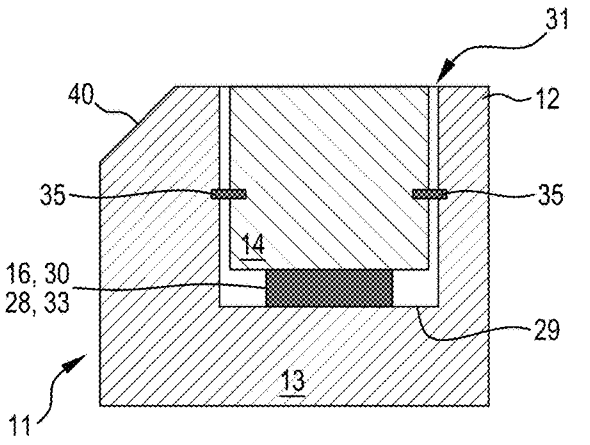
FIG. 6 is a schematic cross-sectional view of the apparatus shown in FIG. 5, in which a user has stopped applying the first pressing force and the humidification chamber is releasably locked in the operating position by first and/or second coupling device(s). The humidification chamber moves from the innermost position as shown in FIG. 5 to the operating position as shown in FIG. 6 under the action of the actuator.

FIG. 6 illustrates the humidification chamber 14 on the base 28 in the operating position.

Figure 3:
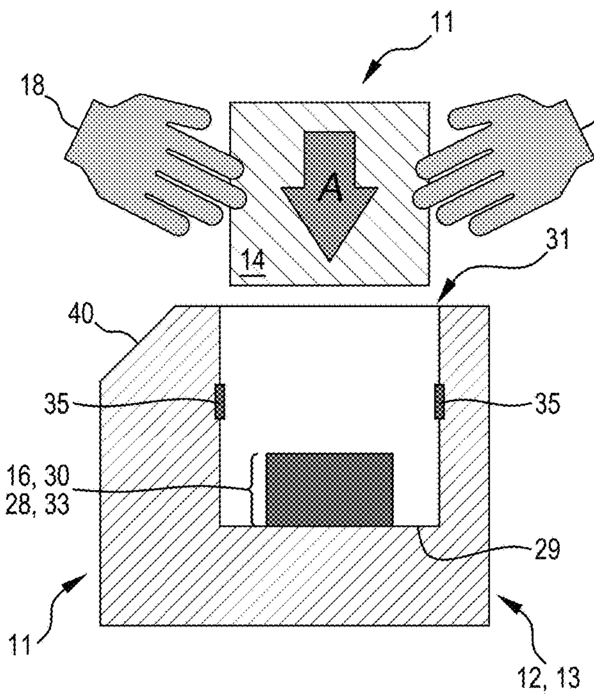
FIG. 3 is a schematic cross-sectional view of the apparatus shown in FIGS. 1 and 2, in which a user is initially loading the humidification chamber into the compartment.
Figure 5:
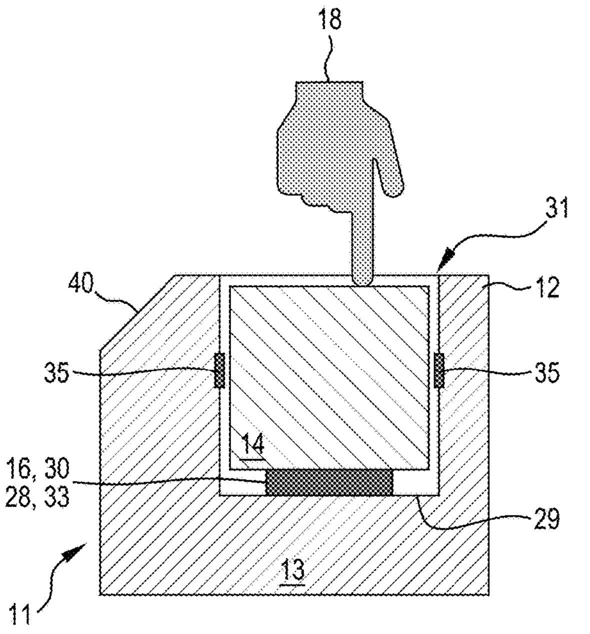
FIG. 5 is a schematic cross-sectional view of the apparatus shown in FIG. 4, in which the first pressing force has moved the humidification chamber from the releasing position inwardly past the operating position into an innermost position (i.e., to a lowermost position) to engage a first coupling device.

FIG. 3 depicts the user 18 manually loading the humidification chamber 14 on the base 28, and FIG. 4 depicts the user 18 applying a first pressing force to the humidification chamber 14 in the direction of arrow A, i.e., toward the floor 29 of the compartment 12. The first pressing force moves the base 28 and the humidification chamber 14 downwardly within the humidification compartment 12 to a lowermost position, as shown in FIG. 5, which is inward of the operating position. By moving the humidification chamber 14 to the lowermost position, the user 18 activates a first coupling device 35.

In other words, the user 18 activates the first coupling device 35 by moving the humidification chamber 14 from the releasing position to the lowermost position. Although not shown in the figures, it will be appreciated that the first coupling device 35 may be operated by the user 18 moving the humidification chamber 14 from the releasing position to any position inward of the releasing position. Another possible modification, which is not shown in the figures, is the first pressing force A could be applied directly to the actuator 16, or indirectly to the actuator 16 via, for example, a handle extending from the base 28 rather than pressing the humidification chamber 14.

Although not shown in the figures, the first coupling device 35 may be a push-latch device having a lug that is received within an opening, for example, the lug may be received within an opening by the base moving inwardly of the operating position to a lowermost position, such as that shown in FIG. 5. Preferred details of the first coupling device 35 are described with reference to FIGS. 9 to 13.

Ideally an indicator emits an output, such as a visual, tactile, or audible output, that makes it known to the user that the first coupling device 35 has been activated. When an output of the indicator has been detected, the user can then cease applying the first pressing force and the humidification chamber will move from the lowermost position to the operating position under the action of the actuator 16 where it is releasably locked within the humidification compartment 12, as shown in FIG. 6.

Figure 7:
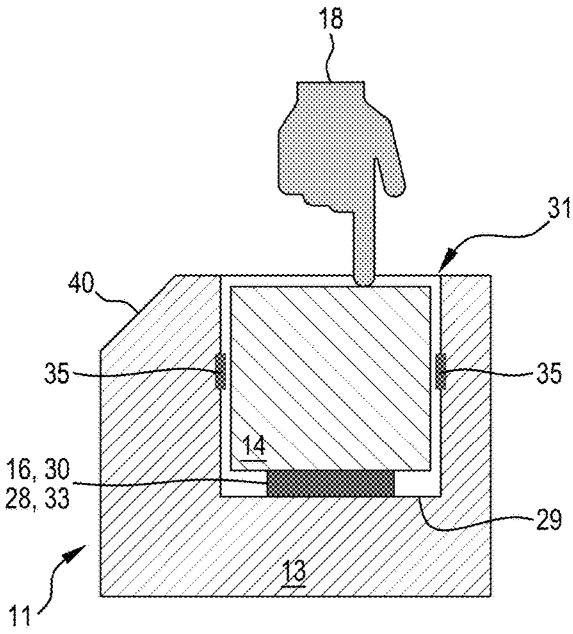
FIG. 7 is a schematic cross-sectional view of the apparatus shown in FIG. 6, in which a user applies a second pressing force in the direction of arrow A to move the humidification chamber inwardly from the operating position to an innermost position which uncouples the first and/or second coupling devices.

In order to remove the humidification chamber 14 from the compartment 12, the user 18 applies a second pressing force in the direction of arrow A, i.e., in the direction toward the floor 29 of the compartment 12, as seen in FIG. 7, which deactivates the first coupling device 35, and allows the actuator 16 to move the base 28 and the humidification chamber 14 upwardly within the humidification compartment 12 in the direction of arrow B, as shown in FIG. 8. In particular, the actuator 16 is arranged to locate the base 28 at an elevated position within the humidification compartment 12 such that the top of the humidification chamber 14 extends above the opening 31 of the humidification compartment 12 by a release distance that may, for example, be a range of 1 to 20 cm and suitably be in the range of 4 to 8 cm. The part of the humidification chamber 14 extending above the opening of the humidification compartment is a gripping section 32 that a user 18 can readily grasp with their fingers to remove the humidification chamber 14 from the compartment 12. The gripping section 32 may be any peripheral portion of an outer wall of the chamber 14 that extends above the opening 32 of the humidification compartment 12. Although not shown in the figures, the gripping section 32 may have any suitable contours including finger recesses and/or undercuts that allow the user 18 to easily handle the humidification chamber 14. Although not shown in the figures, the humidification chamber 14 may also include a handle.

As can best be seen in FIG. 1, the base 28 also includes a heater element 33 that is powered to generate heat. The heater base 34 of the humidification chamber 14 is thermally conductive, and transfers heat from the heater element 33 to the water in the humidification chamber 14 during use, thereby increasing the evaporation of water in the chamber 14 and humidifying the breathable gas stream for delivery to the user 18. However, it will be appreciated that the water in the humidification chamber 14 can be heated via other means. For instance, in one example a heating element may be contained within the humidification chamber 14 and co-operating electrical couplings can be provided on the base 28 and the heating element of the humidification chamber 14. The co-operating electrical couplings are connected when the humidification chamber 14 is positioned on the base 28. In another example the electrical couplings may be provided on a sidewall of the humidification compartment 12 and a sidewall of the humidification chamber 14, and the electrical couplings are connected when the humidification chamber is in the operating position.

The first coupling device 35 acts between the humidification chamber 14 and the compartment 12 and the first coupling device 35 is operable to hold the heater base 34 relative to the heater element 33. This enables the actuator 16 to press the heater element 33 against the heater base 24 to facilitate thermal engagement therebetween. In other words, the actuator 16 may have the dual purpose of moving the humidification chamber 14 from the operating position to the releasing position when the first coupling device 35 is deactivated, and pressing the heater element 33 against the heater base 34 when the first coupling device 35 is activated.

FIGS. 9 to 13 illustrate the details of the first coupling device 35 that acts between the humidification chamber 14 and the humidification compartment 12. The first coupling device 35 has a fixed cam 43 mounted to an inner surface of the humidification compartment 12 that is engaged by a locking member 44 including a lug that is attached to the humidification chamber 14, and the locking member 44 engages the fixed cam 43 when the humidification chamber 14 moves inward and outward of the humidification compartment 12. In the case of the preferred embodiment, the humidification chamber 14 moves upward and downward between the releasing and operating positions, and the locking member 44 is releasably secured to a recessed surface 50 at a distal end 51 of the fixed cam 43, see FIG. 13, when the humidification chamber 14 is in the operating position.

The locking member 44 is resiliently moveable relative to the humidification chamber 14 by way of a biasing member 45 that biases the locking member 44 toward a neutral position. Ideally, the biasing member 45 has a resiliently flexible arm 45 that is attached to the humidification chamber 14 and can flex transversely to the direction of movement of the humidification chamber 14 between the releasing position and the operating position. The resiliently flexible arm 45 is located in a depression 52 in an outer surface of the humidification chamber 14 and may be fixedly attached to the humidification chamber 14. The resiliently flexible arm 45 may be integrally formed with the outer continuous surface of the humidification chamber 14, that is, with no depression, and/or detachably connected to the humidification chamber 14 so that it can be replaced as desired.

Figure 9:
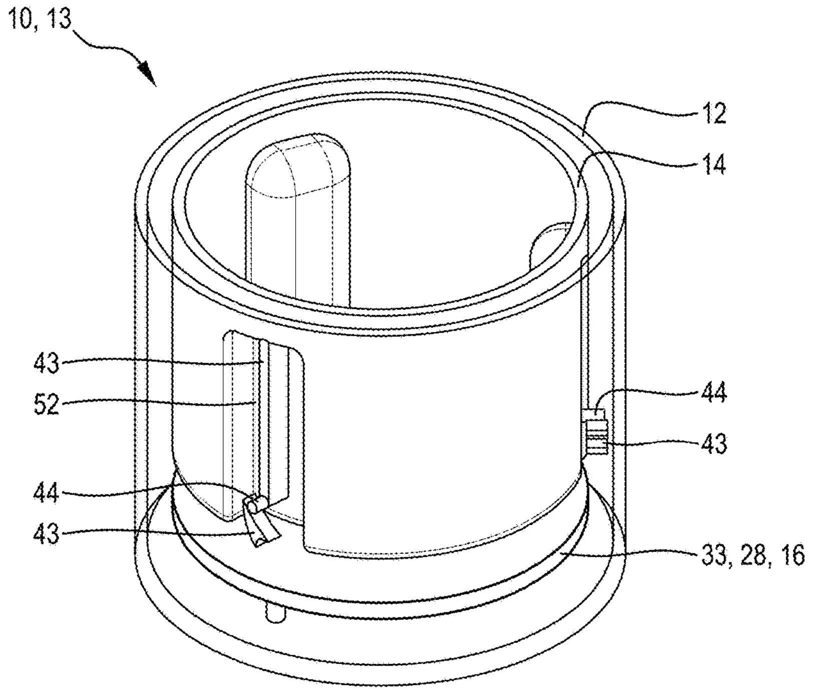
FIG. 9 is a schematic perspective view of the apparatus shown in FIG. 1 according to another example having a first coupling device for releasably locking the humidification chamber in an operating position in the compartment. The wall of the compartment has been illustrated in a transparent manner and a number of details, including features relating to the gas stream and a lid of the chamber have been omitted to maintain clarity of the figure. The humidification chamber is illustrated in a releasing position and three first coupling devices are spaced about the chamber.
Figure 10:
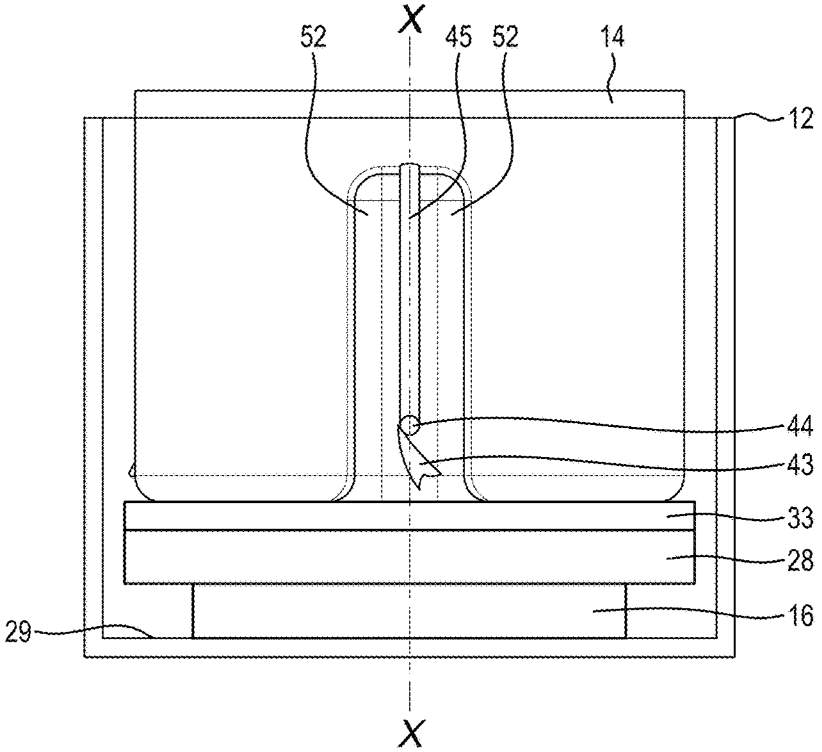
FIG. 10 is side view of the apparatus shown in FIG. 9 with the humidification chamber illustrated in a releasing position.
Figure 12:
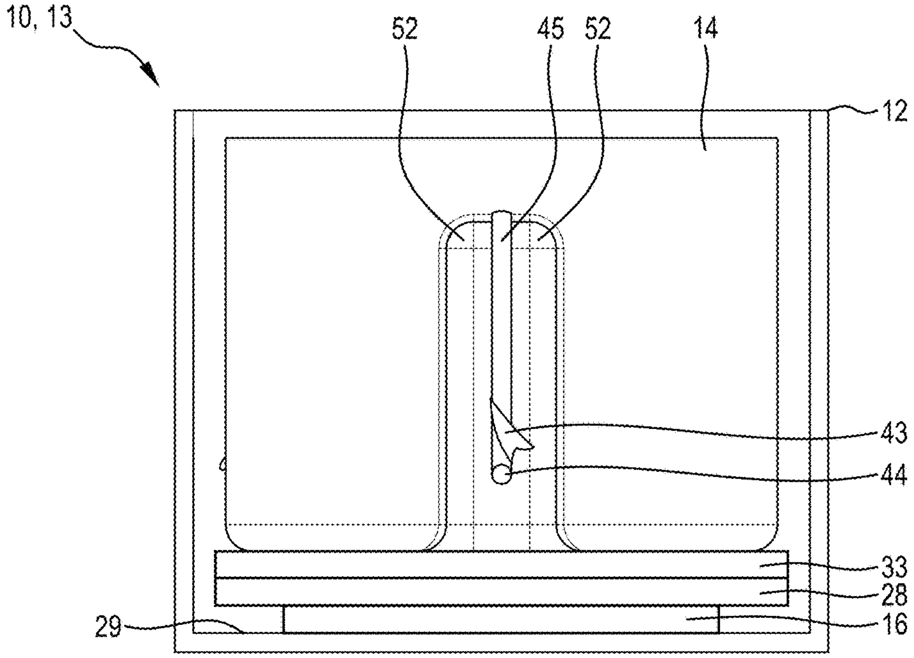
FIG. 12 is a side view of the apparatus shown in FIG. 9 with the humidification chamber in which the humidification chamber has been pushed inward of the operating position to release the first coupling device.

It will be appreciated that the flexible arm 45 may have any initial conformation, including a curved profile such as a curved spring leaf, when the locking member 44 is in the neutral position. However ideally, the arm 45 has a straight longitudinal axis which when the arm 45 is in the neutral position as shown in FIGS. 9, 10 and 12, and which is parallel to the axis X-X in FIG. 13.

The flexible arm 45 may be made of any suitable material. Examples include polymeric material, or a metallic material including a steel leaf spring. In other examples, the biasing member may be one or more of a tension spring or a compression spring (not shown in the Figures).

Figure 13:
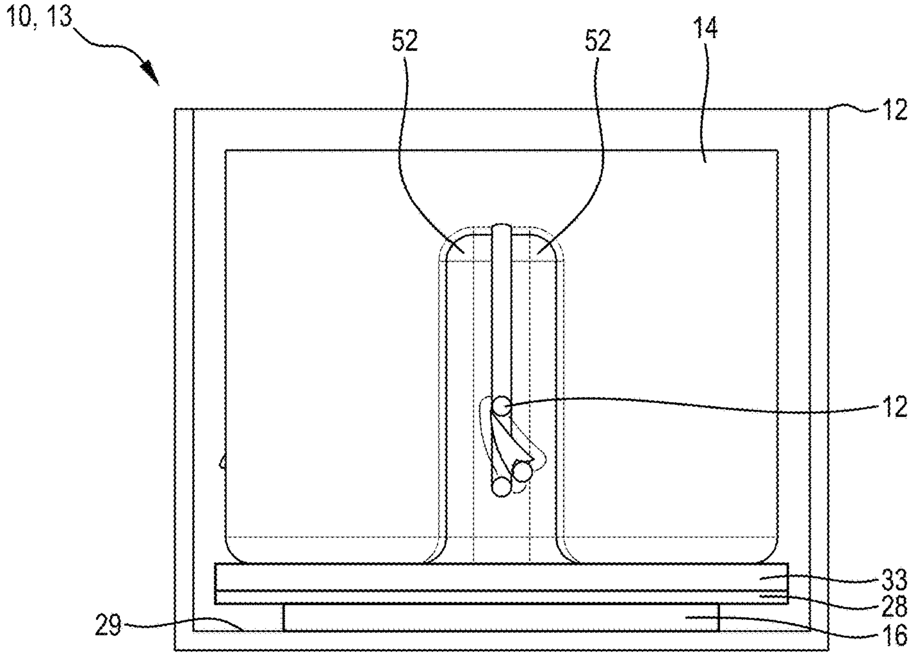
FIG. 13 is a more detailed view of the first coupling device shown in FIG. 9 and the path over which the locking member of the first coupling device moves

The fixed cam 43 has a wedge-shaped body having five working surfaces over which the locking member 44 slides whilst the humidification chamber 14 moves in and out of the humification compartment 12. As can be seen in FIG. 13, the working surfaces of the fixed cam 43 include first and second side surfaces 46 and 47 respectively that extend along the cam 43 from an apex P1 to outer points P2 and P3. The outer point P2 is located further than outer point P3 from the axis X-X. The distal end 51 of the fixed cam 43 has a first end surface 48 extending from the first side surface 46 at point P2 toward the axis X-X, and a second end surface 49 extending from second side surface 47 at point P3. As can best be seen in FIG. 13, the first end surface 48 extends perpendicularly to the axis X-X, and the second end surface 49 extends laterally to the axis X-X. The distal end 51 of the fixed cam 43 also has a retaining formation in the form of a recessed surface 50 between the first and second end surfaces 48 and 49 in which the locking member 44 is releasably disposed when the first coupling device 35 is activated.

As the locking member 44 slides over the surfaces 46, 47, 48 and 49 of the cam 43, the arm 45 resiliently flexes from the axis X-X which holds the locking member 44 against the surfaces 46, 47, 48 and 49 which can act as an indicator to a user on whether the first coupling device 35 has been activated. Specifically, as the locking member 44 moves over the first end surface 48 and into the recessed surface 50, the humidification chamber 14 will move from a position past the operating position upwardly into the operating position.

The sequence by which the humidification chamber 14 is loaded and unloaded from the humidification compartment 12 is as follows. Firstly, a user places the humification chamber 14 into the humidification compartment 12, the locking member 44 will initially contact the first side surface 46 of the cam 43 that faces toward the opening of the humidification compartment 12 as shown in FIGS. 9 and 10. When the locking member 44 contacts the first side surface 46, the gripping section 32 of the humidification chamber 14 will protrude of the humidification compartment 12.

The first coupling device 35 is activated by the user pushing the humidification chamber 14 downward from the releasing position, shown in FIGS. 9 and 10, so that the locking member 44 slides over the first side surface 46 and reaches the point P2. At this stage, the humidification chamber 14 will be located further inward of the humidification compartment 12 than the operating position. The gradient and profile of the first side surface 46, and the friction between the locking member 44 and the first side surface 46 can be selected to provide the desired force and tactical feedback to the user as the humidification chamber 14 is pushed inward. Moreover, the extent to which the arm 45 flexes will impact on the amount of force a user must press on the humidification chamber 14 in order to activate the first coupling device 35. The displacement of the locking member 44 at point P2 from the axis X-X, represented by the arrow D1, will determine the maximum flex of the arm 45, and thus the point at which the resistive force from the arm 45 acting against the humidification chamber 14 moving into the humidification compartment 12 peaks at point P2. Other forces, such as anyone or a combination of the resistive forces from the actuator 16, a second coupling device 30 if present, or biasing of the heater element 33 could also contribute to the resistive force a user may senses when the user pushes the humidification chamber 14 into the humidification compartment 12 to activate the first coupling device 35.

Figure 11:
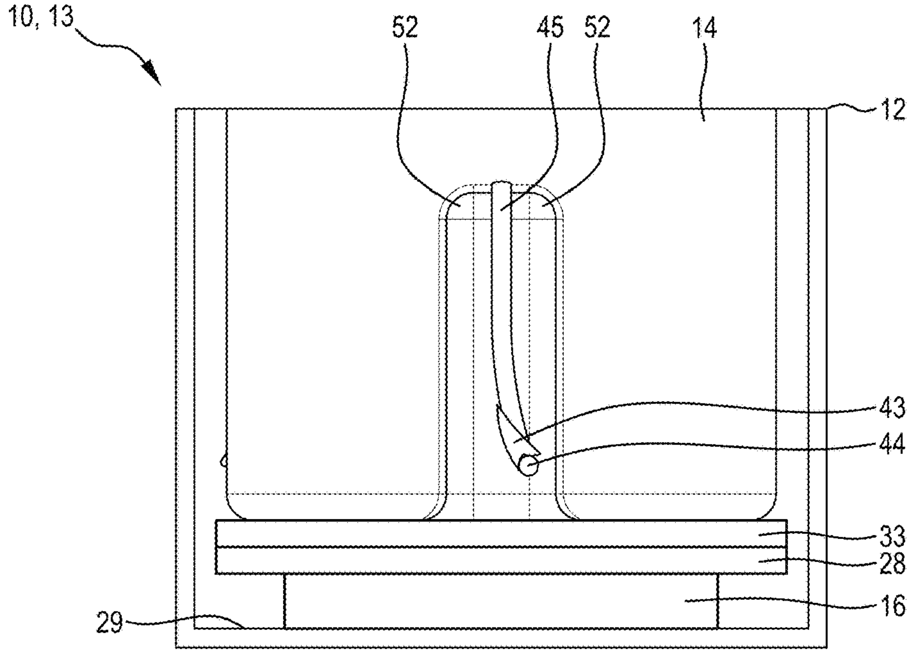
FIG. 11 is a side view of the apparatus shown in FIG. 9 with the humidification chamber in which the first coupling device releasably couples the humidification chamber in an operating position.

Once the locking member 44 has traversed the point P2, and the arm 45 biases the locking member 44 toward the axis X-X and the locking member 44 slides over the first end surface 48 until the locking member 44 is received by the recessed surface 50, as shown in FIG. 11. As described above, the humidification chamber 14 will move upwardly as the locking member 44 is received into the recessed surface 50. The second end surface 49 extends on an acute angle to the edge of the recessed surface 50 in a direction away from the apex P1, thereby providing a barrier or stop against which the locking member 44 abuts. In other words the recessed surface 50 and the second end surface 49 preventing the locking member 44 from inadvertently decoupling or dislodging from the recessed surface 50, thereby activating the first coupling device 35 and locking the humidification chamber 14 in an operative position. The locking member 44 is displaced by a distance D2 from the axis X-X when in the operating position, and a biasing force from the arm 45 presses the locking member 44 against the recessed surface 50 and the second end wall 49. As mentioned above, other resistive forces in a direction toward the opening 31 of the humidification compartment 12, such those of the actuator 16, a second coupling device 30 if present, or biasing of the heater element 33 may also be acting on the humidification chamber 14 when in the operative position as shown in FIG. 11, thereby pressing the locking member 44 into the recessed surface 50.

Ideally, the position of the fixed cam 43 on the humidification compartment 12, the length of the arm 45 and the height of the humidification chamber 14 are selected so that an upper edge of the humidification chamber 14 is flush with the top of the humidification compartment 12 when the first coupling device 45 is activated.

To deactivate the first coupling device 35, the user applies an inward pressing force which moves the humification chamber 14 inwardly in the humidification compartment 12 so that the locking member 44 moves along the second end surface 49 and over point P3, where the locking member 44 is displaced by a distance D3 from the axis X-X. The arm 45 applies a biasing force that moves the locking member 44 from P3 toward the axis X-X. The active force or resistive force of the actuator 16 can them move the humidification chamber 14 from the operating position to the releasing position. When in the releasing position, the locking member 44 is not received by the recessed surface 50, and the locking member 44 may be positioned toward the upper end of the first and second side surfaces 46 and 47.

The length of the second end surface 49 in a direction parallel to the axis X-X determines the distance by the which a user must push the humidification chamber 14 inwardly from the operating position into the humidification compartment 12 to deactivate the first coupling device 35. The curvature and gradient of the second end surface 49, and the friction between the locking member 44 and the second end surface 49 can be selected or adjusted to change the force and tactical feel for a user as the humidification chamber 14 moves into the releasing position.

As can best be seen in FIG. 13, the second end surface 49 extends across the axis X-X from the right-hand side to the left-hand side moving in a direction toward the apex P1. In order to remove the humidification chamber 14 from the humidification compartment 12, the user must lift the humidification chamber 14 which causes the locking member 44 to slide over the second end surface 47 and lateral to the axis X-X by a distance D4 as locking member 44 reaches the upper point P1 of the fixed cam 43. In other words, the first coupling device 35 also provides a resistive force as the humidification chamber 14 is withdrawn from the humidification compartment 12. Thereby preventing the humidification chamber 14 from being inadvertently tipping from the humidification compartment 12. Suitably, the resistive force for removing the humidification chamber 14 is less than the resistive force for locating the humidification chamber 14 in the operating position, that is D4 is less than D1 from the axis X-X.

As can be seen in FIG. 9, a number of the first coupling devices 35 can be located about the perimeters of the humidification chamber 14 and the humidification compartment 12. FIG. 9 shows three of the first coupling devices 35 even spaced about the humidification chamber 14 and humidification compartment 12.

Although not illustrated in the Figures, the position of the fixed cam 43 and the resiliently moveable locking member 44 can be reversed from that shown in the Figures. For example, the fixed cam 43 can be arranged on the humidification chamber 14 with the apex P1 toward a bottom wall of the humidification chamber 14 and the recessed surface 50 for receiving the locking member 44 facing toward the top of the humidification chamber 14. The arm 45 may then be attached to an inside surface of the humidification compartment 12 in which the arm 45 extends upwardly from a point of attached to the compartment 12 and the locking member 44 may be positioned toward a distal end of the arm 45.

The embodiment illustrates in FIGS. 9 to 13 illustrates the locking member 44 being mounted on a resiliently flexible arm 45 that flexes in a plane approximately tangential to the wall of the humification chamber 14. Another variation, not illustrated in the Figures, is that the locking member 44 may resiliently move in direction toward and/or away from walls of the humidification compartment 12 and the humidification chamber 14. According to this variation, instead of having working surfaces of the fixed cam 43 arranged laterally to walls of the humidification compartment 12 and humidification chamber 14, the working surfaces of the cam 43 could be arranged at an acute angle to the wall of the humidification compartment 12 and the resiliently moveable locking member 44 and the arm flexible arm 45 could move toward and/or away from the wall of the humidification compartment 12. In the example where the humidification compartment has a circular cross-section, the arm may flex in radial direction.

If desired, one or more of the flexible arm 45, locking member 44, fixed cam 43 and be removable attached to the respective humidification compartment 12 and/or the humidification chamber 14.

Optionally, the apparatus 11 may also include a second coupling device 30 that acts to lock the actuator 16 and thus the base 28, when the humidification chamber 14 is the operating position. The second coupling device 30 may be provided in addition to, or instead of, the first coupling device 35. However, in the preferred embodiment, only the first coupling device 35 is provided.

The first coupling device 35 and/or the second coupling device 30 may comprise any co-operating connectors including: a sliding connector, a screw connector, a bayonet connector, a magnet connector, a push-latch connector, a male-female interference fit connector, and a snap fit connector.

In addition, the apparatus may have locator formation, not shown in the Figures, that must be aligned in order for the humidification compartment 12 to receive the humidification chamber 14 and allow the first coupling device 35 to be activated. The locator formation may be required when the humidification chamber 14 and the humidification compartment 12 have rounded cross-sections as shown in FIGS. 9 to 13. However, when the humidification compartment 14 and humidification chamber 12 have rectangular cross-sections, a locator formation may not be required.

The apparatus 11 may also include a sealing assembly for sealing the upper opening 31 of the humidification compartment 12 when the humidification chamber 14 is in the operating position. The main reason for forming a seal between the humidification compartment 12 and the humidification chamber 14 is to minimize leaks from the flow path. Any leakage of the flow path will result in a pressure drop in the gas stream, which in turn means that the blower must consume more power to maintain the desired pressure of the gas stream being delivered to the user. Another reason for sealing the humidification compartment 12 is to dampen noise generated by the blower 17 and noise generated by the gas stream passing through the apparatus 11. There are several possible sealing assemblies for sealing the humidification compartment 12.

Figure 2:
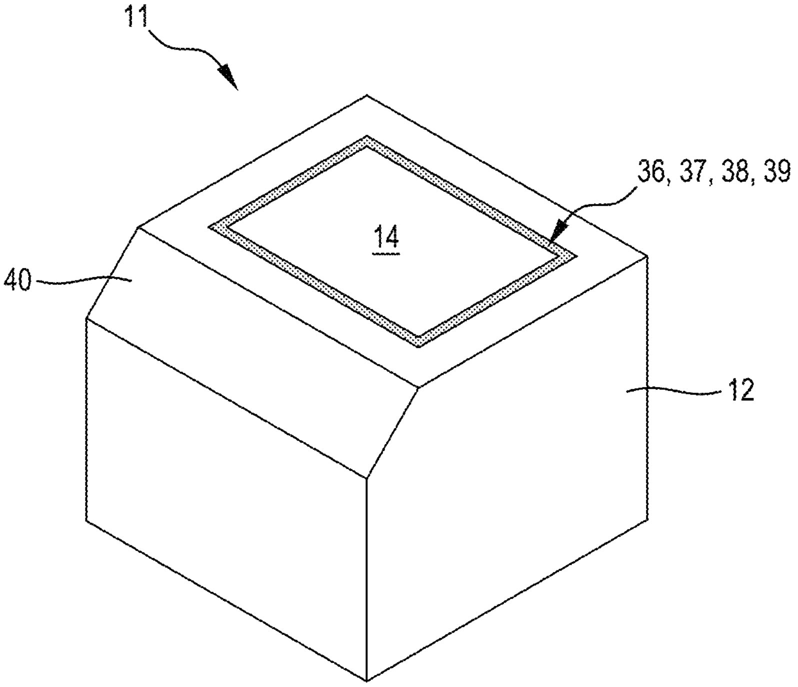
FIG. 2 is a schematic perspective view of the apparatus shown in FIG. 1 in which the humidification chamber is in the operating position where the top of the humidification chamber lies flush with the top of the humidification compartment.
Figure 14:
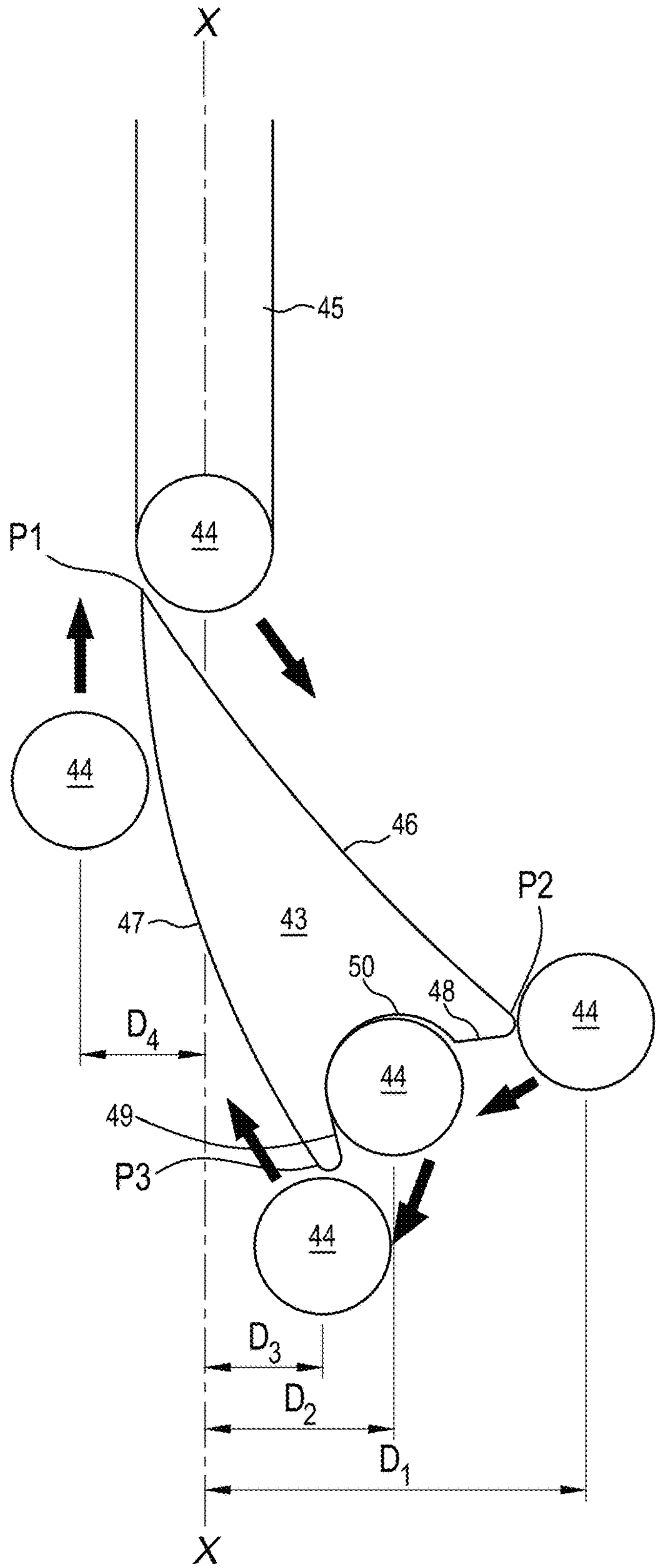
FIG. 14 is a schematic perspective view of the apparatus shown in FIG. 8 according to one example, in which the humidification chamber is in the releasing position and has a first sealing member about an upper portion the chamber.
Figure 15:
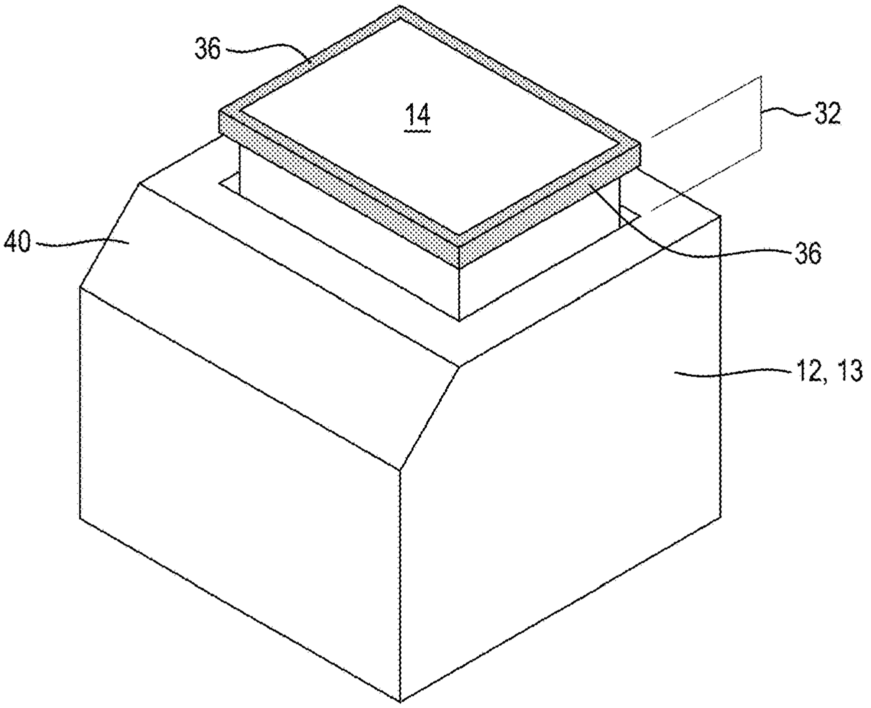
FIG. 15 is a schematic perspective view of the apparatus shown in FIG. 8 according to another example, in which the humidification chamber is in the releasing position and has a second sealing member about an opening of the humidification compartment.
Figure 16:
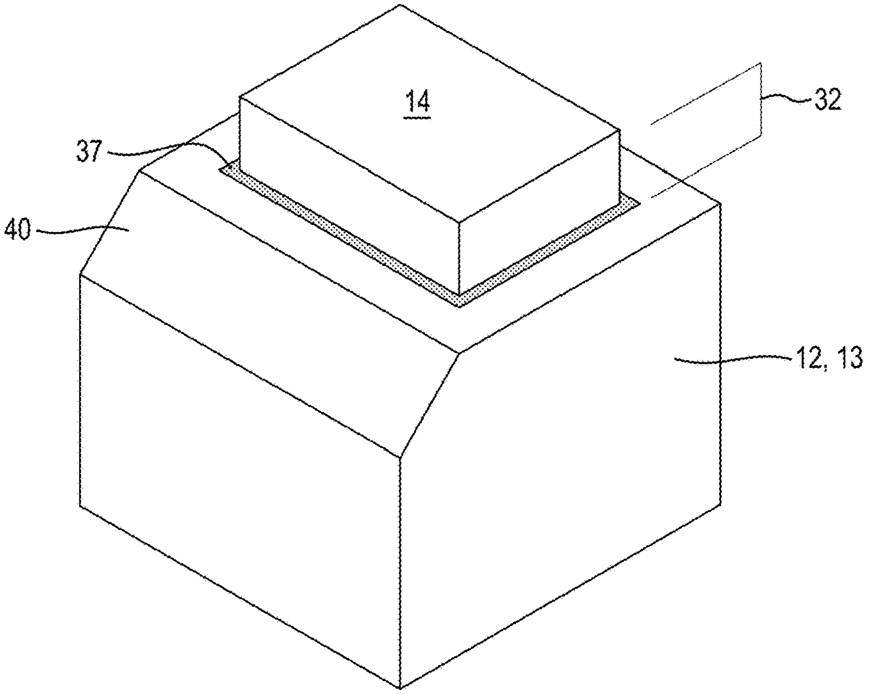
FIG. 16 is a schematic perspective view of the apparatus shown in FIG. 8 according to another example, in which the humidification chamber is in the releasing position and has a first sealing member about an upper portion of the humidification chamber and a second sealing member about an opening of the humidification compartment.

FIGS. 14 to 16 schematically illustrate three examples, in which the sealing assembly acts between an upper portion of the humidification chamber and a corresponding upper portion of the humidification compartment 12. Specifically, FIG. 14 is an example of the sealing assembly including a chamber seal 36 that extends about the perimeter of the humidification chamber 14. The chamber seal 36 is displaced above the opening 31 of the compartment 12 when the humidification chamber 14 is in the releasing position. However, when the chamber 14 is in the operating position as shown in FIG. 2, the chamber seal 36 engages an upper portion of the compartment 12 in order to seal the opening 31 of the compartment 12.

FIG. 15 is an example of the sealing assembly including a compartment seal 37 that extends about a perimeter of the opening 31 of the compartment 12. When the humidification chamber 14 is in the operating position, as shown in FIG. 2, the compartment seal contacts and seals against a side wall of the chamber 14, thereby sealing the compartment 12.

FIG. 16 is an example of a sealing assembly including an inner seal 38 attached to the chamber 14, and an outer seal 39 attached to the opening 31 of the compartment 12. When the humidification chamber 14 is in the operating position, as shown in FIG. 2, the inner and outer seals 38 and 39 can engage to seal the compartment 12.

Figure 17:
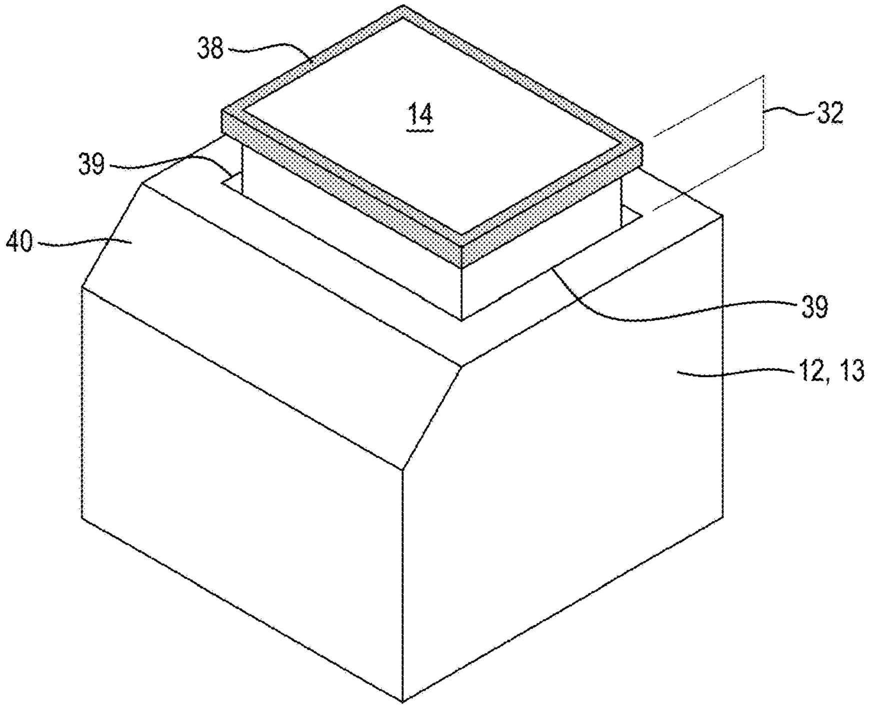
FIGS. 17, 18 and 19 are schematic cross-sectional views of the apparatus shown in FIGS. 1 to 13 according to examples in which upper surfaces of the humidification chamber and compartment are arranged either vertically, at an angle to the vertical, or horizontally respectively. The first and/or second sealing members illustrated in FIGS. 14 to 16 may be arranged on the vertical, angles or horizontal surfaces.

FIG. 17 is a schematic cross-sectional view of any one of the examples in FIGS. 14 to 16.

Figures 18, 19, 20:
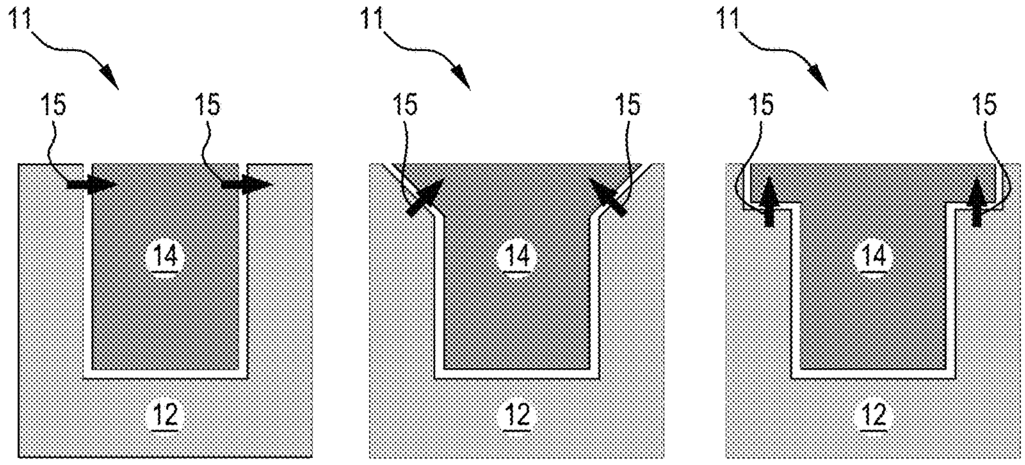

FIG. 18 is an alternative configuration of the upper portions of the humidification chamber 14 and the humidification compartment 12 that are arranged at an angle to the vertical. As a result, movement of the humidification chamber 14 upwardly and in particular, downwardly into the compartment 12 enables either one or both of the chamber seal 36 or the compartment seal 37 to be engaged with a degree of force on the respective seal 38 and 39, thereby potentially improving sealing of the compartment 12.

FIG. 19 is an alternative configuration of the upper portions of the humidification chamber 14 and the humidification compartment 12 that includes a horizontal component on either one or both of the chamber seal 36 or the compartment seal 37. Downward movement of the chamber 14 in the compartment 12 into the operating position can, thereby readily impart forces on the seals 36 and 37, which may improve the engagement of the seals and in turn, sealing of the compartment 12.

As described above with reference to FIG. 1, when the humidification chamber 14 is in the operating position, the inlet port 24 of the humidification compartment 12 connects to the inlet 25 of the humidification chamber 14, and the outlet port 27 of the humidification compartment 12 connects to an outlet 26 of the humidification chamber 14. The inlet and outlet ports 24 and 27 of the humidification compartment 12 may include first seals (not shown in the figures), and the inlet 25 and the outlet 26 of the humidification chamber 14 may include second seals (not shown in the figures).

The seals may be flexible, rigid or inflated seals that sealingly engage when the humidification chamber is in the operating position, and disengage when the humidification chamber is in the releasing position. Depending on the configuration of the walls of the humidification chamber and the humidification compartment, the first and second seals may be arranged on upright surfaces as depicted in FIG. 17, on inclined sur faces as depicted in FIG. 18, and on horizontal surfaces as depicted in FIG. 19. The arrows in FIGS. 17 to 19 indicating the direction of flow of the gas stream from the outlet port to the inlet port respectively.

The first and second seals for sealing the inlet port 27 and outlet port 24 of the humidification compartment 12 with the inlet and outlet of the humidification chamber can be used in combination with, or instead of, the sealing assemblies for sealing the humidification compartment as described above with reference to FIGS. 14 to 16. Similarly, the sealing assemblies described with reference to FIGS. 14 to 16 can be used without the inlet and outlet ports of the compartment being completely sealed with the inlet and outlets of the humidification chamber.

Moreover, the sealing assembly may also include flow path sealing members (not shown in the figures) that seal the connection between the outlet port 24 of the humidification compartment 12 and the chamber inlet 25. For instance, the sealing assembly may include an outlet port sealing member at the outlet port 24 of the humidification compartment, and an inlet sealing member at the chamber inlet 25 that sealingly engage when the humidification chamber 14 is in the operating position.

The outlet port sealing member and the inlet sealing member may extend about the outlet port 24 of the compartment and the chamber inlet 25 respectively.

In addition, the path sealing members may include an inlet port sealing member at the inlet port of the humidification compartment, and an outlet sealing member at the outlet of the humidification chamber that sealingly engage when the humidification chamber is in the operating position.

The inlet port sealing member and the outlet sealing member may extend about the inlet port 27 of the compartment and the chamber outlet 26.

The outlet and inlet ports 24 and 27 of the compartment 12, and the chamber inlet 25 and chamber outlet 26 may be arranged in either: i) the vertical plane as depicted by the embodiment shown in FIG. 17, ii) the horizontal plane as depicted by the embodiment shown in FIG. 19, or iii) at an angle to the vertical and horizontal as depicted by the embodiment shown in FIG. 18.

Although not shown in detail in the figures, the heater base and/or the base 28 may include first locators that inter-fit with second locators on a bottom wall of the humidification chamber 14 to facilitate relative positioning of the humidification chamber 14 on the base 28. In one example, the first locator may include a central peg extending upwardly from the heater element and/or base, and the heater base of the humidification chamber may have a second locator including a recess which cooperates with the central peg. Either one or both of the central peg and the recess may have a tapered profile which allows initially for coarse alignment of the humidification chamber 14, followed by finer alignment as the peg is received deeper within the recess.

In another example, the first locators may include barrier sections about the base 28 or a fence about a perimeter of the base 28 within which the humidification chamber 14 is located.

FIGS. 1 and 3 to 8 illustrate the actuator 16 as one or more biasing elements located between the floor 29 of the humidification compartment 12 and the base 28. However, it will be appreciated that the actuator 16 can be located at other parts of the apparatus. For example, the actuator may be mounted to one or more of: i) the bottom of the humidification chamber 14, ii) the side wall of the humidification compartment 12, and iii) the sealing assemblies, for moving the humidification chamber upwardly.

FIGS. 2, 14, 15 and 18 each include an operator panel 40 or display comprising a circle, triangle and square. It is to be noted that the circle, triangle and square have been included to represent the region in which a display panel or control switches could be located. However, it will be understood that the display panel or control switches are by no means limited to the geometric shapes of a circle, triangle or square.

Those skilled in the art of the present invention will appreciate that many variations and modifications may be made to the preferred embodiment without departing from the spirit and scope of the present invention.

Although not shown in detail in the figures, the humidification chamber may include a top wall that is itself a removable cover or includes removable panels for pouring water into the chamber, or for cleaning the chamber.

In addition, although not shown in the figures, the top wall of the humidification chamber 14 may include a depression in an outer surface that resembles an enlarged operating button, which in turn provides the user with a visual clue that the chamber 14 can be pressed, and in turn moved upward and downward.

In the claims which follow, and in the preceding description, except where the context requires otherwise due to express language or necessary implication, the word "comprise" and variations such as "comprises" or "comprising" are used in an inclusive sense, i.e. to specify the presence of the stated features but not to preclude the presence or addition of further features in various embodiments of the apparatus and method as disclosed herein.

In the foregoing description of preferred embodiments, specific terminology has been resorted to for the sake of clarity. However, the invention is not intended to be limited to the specific terms so selected, and it is to be understood that each specific term includes all technical equivalents which operate in a similar manner to accomplish a similar technical purpose. Terms such as "front" and "rear", "inner" and "outer", "above" and "below", "upper" and "lower" and the like are used as words of convenience to provide reference points and are not to be construed as limiting terms. The terms "vertical" and "horizontal" when used in reference to the humidification apparatus throughout the specification, including the claims, refer to orientations relative to the normal operating orientation.

Furthermore, the invention has been described in connection with what are presently considered to be the most practical and preferred embodiments, it is to be understood that the invention is not to be limited to the disclosed embodiments, but, on the contrary, is intended to cover various modifications and equivalent arrangements included within the spirit and scope of the invention. Also, the various embodiments described above may be implemented in conjunction with other embodiments, for example, aspects of one embodiment may be combined with aspects of another embodiment to realize yet other embodiments. Further, each independent feature or component of any given assembly may constitute an additional embodiment.

Reference numeral table

| | |
|---|---|
| respiratory device | 10 |
| humidification apparatus | 11 |
| humidification compartment | 12 |
| housing | 13 |
| humidification chamber | 14 |
| gas stream | 15 |
| actuator | 16 |
| blower | 17 |
| user | 18 |
| air intake | 21 |
| passageway | 22 |
| conduit | 23 |
| outlet port | 24 |
| chamber inlet | 25 |
| chamber outlet | 26 |
| inlet port | 27 |
| base | 28 |
| floor | 29 |
| second coupling device | 30 |
| upper opening | 31 |
| gripping section | 32 |
| heater element | 33 |
| heater base | 34 |
| first coupling device | 35 |
| chamber seal | 36 |
| compartment seal | 37 |
| inner seal | 38 |
| outer seal | 39 |
| operator panel | 40 |
| housing outlet port | 41 |
| flow path | 42 |
| locking member/lug | 43 |
| fixed cam | 44 |
| biasing member/arm | 45 |
| first side surface (of fixed cam) | 46 |
| second side surface (of fixed cam) | 47 |
| first end surface | 48 |
| second end surface | 49 |
| recessed surface | 50 |
| distal end | 51 |

The invention claimed is:

1. A humidification apparatus comprising:

an apparatus outlet port that is configured to enable delivery of gas to a patient;

a removable humidification chamber configured to contain water;

a humidification compartment that receives the removable humidification chamber;

a flow path that is configured to direct a gas stream to the apparatus outlet port; and an actuator that is configured to move the removable humidification chamber between an operating position and a releasing position, in the operating position, the removable humidification chamber is received by the humidification compartment and the removable humidification chamber forms a portion of the flow path through the humidification apparatus, in the releasing position, the removable humidification chamber is displaced outwardly from the operating position and is removable from the humidification apparatus, moving the removable humidification chamber into the operating position comprising movement of the removable humidification chamber in a first direction and moving the removable humidification chamber into the releasing position also comprising movement of the removable humidification chamber in the first direction.

2. The humidification apparatus of claim 1, wherein the removable humidification chamber comprises a thermally conductive heater base and the humidification compartment comprises a heater element, wherein the actuator presses the heater element against the thermally conductive heater base when the removable humidification chamber is in the operating position.

3. The humidification apparatus of claim 1, wherein the flow path is sealed and extends through the removable humidification chamber to the apparatus outlet port or a gas stream conduit, when the removable humidification chamber is in the operating position, and the flow path is broken when in the releasing position.

4. The humidification apparatus of claim 1, wherein the actuator provides an active force or resistance in a direction towards an opening of the humidification compartment, wherein force applied to the removable humidification chamber in a direction against the actuator moves the removable humidification chamber from the releasing position to the operating position.

5. The humidification apparatus of claim 1, wherein the removable humidification chamber moves a release distance between the operating position and the releasing position, wherein the release distance is between 1 cm and 20 cm.

6. The humidification apparatus of claim 1, wherein the removable humidification chamber does not protrude from the humidification compartment when the removable humidification chamber is in the operating position.

7. The humidification apparatus of claim 1, wherein the removable humidification chamber comprises a gripping section used while manually removing the removable humidification chamber from the humidification compartment, the gripping section protrudes from the humidification compartment when the removable humidification chamber is in the releasing position, the gripping section is located within the humidification compartment when the removable humidification chamber is in the operating position, the gripping section comprises a portion of an outer side wall of the removable humidification chamber that extends outwardly of an opening of the humidification compartment, and the gripping section comprises a higher friction inducing surface relative to adjacent surfaces of the removable humidification chamber.

8. The humidification apparatus of claim 1, wherein the removable humidification chamber moves inwardly of the operating position when a pressing force is applied, and the removable humidification chamber moves from the operating position to the releasing position when the pressing force is removed.

9. The humidification apparatus of claim 1, wherein the removable humidification chamber moves from the releasing position into the operating position when a pressing force is applied to the removable humidification chamber.

10. The humidification apparatus of claim 9, further comprising at least one coupling device between the removable humidification chamber and the humidification compartment, wherein the at least one coupling device is operable to releasably lock the removable humidification chamber in the operating position.

11. The humidification apparatus of claim 10, wherein the pressing force moves the removable humidification chamber from the releasing position to the operating position and activates the at least one coupling device to releasably lock the removable humidification chamber in the operating position.

12. The humidification apparatus of claim 1, wherein the humidification apparatus further comprises a blower configured to generate the gas stream, wherein the flow path extends from the blower to the apparatus outlet port.

13. The humidification apparatus of claim 12, wherein the humidification compartment comprises a flow path outlet port and the blower comprises a blower outlet port, wherein the flow path outlet port is in communication with the blower outlet port, and the apparatus outlet port can be either the flow path outlet port or a humidification chamber outlet port.

14. The humidification apparatus of claim 12, wherein the flow path comprises a first flow path portion extending from the blower to the removable humidification chamber, wherein a first seal seals the first flow path portion to the removable humidification chamber when in the operating position, and the first seal no longer seals the first flow path portion to the removable humidification chamber when in the releasing position.

15. The humidification apparatus of claim 14, wherein the flow path further comprises a second flow path portion extending to the apparatus outlet port, wherein a second seal seals the second flow path portion to the removable humidification chamber when in the operating position, and the second seal no longer seals the second flow path portion to the removable humidification chamber when in the releasing position.

16. The humidification apparatus of claim 1, further comprising a sealing assembly that seals the flow path, the sealing assembly extending between the humidification compartment and the removable humidification chamber when the removable humidification chamber is in the operating position.

17. The humidification apparatus of claim 16, wherein the sealing assembly provides a seal between an opening of the humidification compartment and the removable humidification chamber when the removable humidification chamber is in the operating position.

18. The humidification apparatus of claim 17, wherein the sealing assembly comprises a chamber sealing member extending about an upper part of an outer wall of the removable humidification chamber, the chamber sealing member sealingly engaging an inner wall of the humidification compartment when the removable humidification chamber is in the operating position.

19. The humidification apparatus of claim 18, wherein the sealing assembly further comprises a compartment sealing member extending about an upper part of a side wall defining an opening of the humidification compartment, the compartment sealing member sealingly engaging the removable humidification chamber when the removable humidification chamber is in the operating position.

20. The humidification apparatus of claim 19, wherein the chamber sealing member and the compartment sealing member sealingly engage when the removable humidification chamber is in the operating position.

21. A humidification apparatus comprising a housing, the housing defining a humidification compartment, the humidification compartment being configured to receive a removable humidification chamber, the removable humidification chamber defining a liquid reservoir, the removable humidification chamber configured to be in fluid communication with a humidification apparatus outlet port, the humidification apparatus outlet port being capable of delivering gases to a patient, the removable humidification chamber being movable between an operating position and a releasing position, the removable humidification chamber being removable from the housing when the removable humidification chamber is in the releasing position, moving the removable humidification chamber between the operating position and the releasing position comprises applying a force in a first direction and moving the removable humidification chamber between the releasing position and the operating position also comprises applying a force in the first direction, and an actuator that is operated when the force is applied in the first direction.

22. The humidification apparatus of claim 21, wherein the force activates a first coupling device to releasably lock the removable humidification chamber in the operating position.

23. The humidification apparatus of claim 22, wherein the force moves the removable humidification chamber inwardly of the operating position to activate the first coupling device when moving the removable humidification chamber between the releasing position and the operating position.

24. The humidification apparatus of claim 22, wherein the first coupling device is configured to be unlocked by action of the force in the first direction when the first coupling device is in the operating position.

* * * * *